(12) United States Patent
Spatola et al.

(10) Patent No.: US 10,342,997 B2
(45) Date of Patent: Jul. 9, 2019

(54) DYNAMIC BEAM'S EYE VIEW OF PROTON THERAPY IRRADIATION SHOWN IN ANATOMICAL CONTEXT

(71) Applicant: Varian Medical Systems, Inc., Palo Alto, CA (US)

(72) Inventors: Brian Spatola, Huntington Beach, CA (US); Richard Kane, Los Altos, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 746 days.

(21) Appl. No.: 14/573,906

(22) Filed: Dec. 17, 2014

(65) Prior Publication Data

US 2016/0175617 A1 Jun. 23, 2016

(51) Int. Cl.
*A61N 5/00* (2006.01)
*A61N 5/10* (2006.01)

(52) U.S. Cl.
CPC ......... *A61N 5/1071* (2013.01); *A61N 5/1049* (2013.01); *A61N 5/1075* (2013.01); *A61N 2005/1062* (2013.01); *A61N 2005/1074* (2013.01); *A61N 2005/1087* (2013.01)

(58) Field of Classification Search
CPC ..... A61B 18/12; A61B 18/1815; A61B 18/20; A61B 2018/00577; A61B 2034/254; A61B 2090/374; A61B 34/25; A61B 5/015; A61B 5/055; A61B 5/7435; A61B 8/13; A61B 8/465; A61F 7/00; A61N 5/00; A61N 5/1084; A61N 7/00; A61N 7/02; F04C 2270/041; G01R 33/4808; G01R 33/4814; G01R 33/546; G06F 19/3406; G06F 3/0484
USPC ............................................................ 600/1
See application file for complete search history.

(56) References Cited

U.S. PATENT DOCUMENTS

| | | | | |
|---|---|---|---|---|
| 6,222,544 B1* | 4/2001 | Tarr | ...................... | A61N 5/103 128/845 |
| 7,831,289 B2* | 11/2010 | Riker | ................... | A61N 5/1031 378/65 |
| 8,073,104 B2* | 12/2011 | Yan | ...................... | A61N 5/1049 378/65 |
| 8,106,371 B2* | 1/2012 | Fujii | .................... | A61N 5/1044 250/492.3 |
| 8,559,596 B2* | 10/2013 | Thomson | .............. | G06T 7/0014 378/20 |
| 8,694,157 B2* | 4/2014 | Wenderow | ........... | A61B 5/7475 600/523 |
| 2014/0336438 A1* | 11/2014 | Bharat | ................. | A61N 5/1031 600/1 |

(Continued)

*Primary Examiner* — Samuel G Gilbert (57) ABSTRACT

System and method of dynamically presenting visual representations of a target volume in an anatomical context to an operator-user of a charged particle radiation therapy system. The visual representations are integrated as a part of a treatment console graphical user interface (GUI) and presented as a part of a holistic view of treatment information. The visual representations are digitally reconstructed radiographs (DRRs) constructed based on anatomical images captured before the therapy session, or alternatively during a treatment session using an imaging system attached to the radiation treatment system. In an online mode, the on-screen visual representations are rendered in synchronization with the irradiation delivery process.

20 Claims, 5 Drawing Sheets

(56) References Cited

U.S. PATENT DOCUMENTS

2015/0169836 A1\* 6/2015 Vahala .................... A61N 7/02
600/411

\* cited by examiner

DYNAMIC BEAM'S EYE VIEW OF PROTON THERAPY IRRADIATION SHOWN IN ANATOMICAL CONTEXT

TECHNICAL FIELD

Embodiments of the present disclosure relate generally to medical devices, and more particularly, to user interfaces for radiation therapy devices.

BACKGROUND

Proton therapy is an advanced radiation treatment using a proton beam to destroy diseased cells while effectively sparing surrounding healthy tissue. The chief advantage of proton therapy over other conventional radiotherapies, such as X-ray or neutron radiation therapy, is the ability to administer treatment dosages three-dimensionally by specifying the depth of radiation due to low proton beam penetration. The proton beam can be focused directly on a target volume (e.g., cancerous tissues) and the inadvertent harm to the surrounding healthy tissues can be effectively restricted. This enables a proton therapy treatment to localize the radiation dosage more precisely than other types of external beam radiotherapy.

During the operation of a typical proton beam irradiation system, a particle accelerator, such as a cyclotron, is used to generate a beam of protons for example from an internal ion source. The protons in the beam are accelerated and guided through a beam-line by a combination of magnetic fields and electric fields. Eventually, a proton beam is output through a scanning nozzle to irradiate a target volume or area of a patient's body. Particularly, in proton pencil beam scanning, a planning target volume (PVT) of a treatment site is irradiated as a series of layers and proton irradiation is delivered one layer at a time.

A proton radiation treatment system usually is connected to a computing device so that a therapist conducting a treatment session can interact with the treatment system. Through a computer implemented user interface, for example, the computing device can receive the therapist's instructions to control the treatment system operations as well as present the operational statuses of various components in the treatment system.

In general, it is desirable that the anatomy of an irradiation target volume can be visually presented to the therapist before, during and after an irradiation therapy session for purposes of preview, verification, monitoring, and assessment of the therapy process. Such visualization capabilities are common to X-ray radiation treatment systems. For example, a beam's eye view with a view angle oriented along the desired beam angle can be generated by exposing a high energy film or an electronic portal imaging device (EPID) with the treatment X-ray itself after it passes through the patient's body and any beam modifiers, e.g., an amplifier.

However, in proton as well as other charged particle radiation therapies, there is a lack of particles passing through a patient's body and so the information to produce a dynamic anatomical visualization is not readily available. As a consequence, a proton radiation therapist is incapable of conveniently visualizing a treatment site per treatment plan prior to the treatment, and incapable of monitoring the irradiation progress during the treatment, or visualizing and evaluating the results of irradiation after the treatment.

SUMMARY OF THE INVENTION

Provided herein are a mechanism and process offering a radiation therapist an anatomical sense of irradiation beam placement as regards to a particle radiation treatment session to facilitate quality assurance and therapy planning.

Embodiments of the present disclosure employ a computer implemented method of dynamically presenting anatomical visualizations of a target volume for proton irradiation within a treatment console graphical user interface (GUI). For a particular treatment session, a set of digitally reconstructed radiographs (DRRs) of the target volume are presented, with each DRR corresponding to an irradiation layer of the target volume. The DRRs are generated based on anatomical images obtained before a treatment session, or alternatively during a treatment session using an imaging system attached to the radiation treatment system. According to various embodiments, a contour line delineating the target volume is superimposed on an anatomical presentation thereof rendered on the GUI. In an online mode, the set of DRRs are displayed sequentially in synchronization with the irradiation beam scanning process. Specifically, a currently displayed DRR represents the anatomy of a currently irradiated layer. Thereby, a therapist is advantageously provided with a visualization of the irradiation process layer-by-layer in an anatomical context.

In one embodiment of the present disclosure, a computer implemented method of providing visual representations of radiation therapy processes includes rendering an on-screen graphical user interface (GUI) for display on a display device communicably coupled to a particle radiation apparatus. The on-screen GUI is configured to present patient information pertinent to a therapy session and present operational statuses of the particle radiation apparatus with respect to the therapy session. An image including an anatomical representation of an irradiation target volume is also presented within the on-screen GUI.

In one embodiment of the present disclosure, the irradiation of the BEV area could be visualized not just during irradiation, but also as a preview before treatment or as a post-treatment review (e.g. as a video or slide show).

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention. Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Notation and Nomenclature:

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or display devices. When a component appears in several embodiments, the use of the same reference numeral signifies that the component is the same component as illustrated in the original embodiment.

Dynamic Beam's Eye View of Proton Therapy Irradiation Shown in Anatomical Context Overall, provided herein are a system and a method of dynamically presenting visual representations of a target volume in an anatomical context to an operator-user of a charged particle radiation therapy system. The on-screen visual representations are integrated as a part of a treatment console graphical user interface (GUI) and presented as a part of a holistic view of treatment information. In accordance with various embodiments, the on-screen visual representations are digitally reconstructed radiographs (DRRs) created based on anatomical images captured before the therapy session. In an "online" mode, the on-screen visual representations are rendered in synchronization with the irradiation delivery process.

Although embodiments of the present disclosure are described with reference to proton radiation therapy systems, and more specifically, to pencil proton beam scanning systems, it will be appreciated by those skilled in the art that the present disclosure can be practiced on any type of therapy system that utilizes charged particle radiation, such as $He^{2+}$ or $C^{6+}$ particles. Further, it will be appreciated that the present disclosure is not limited to any specific configuration of a charged particle radiation system.

Figure 1:
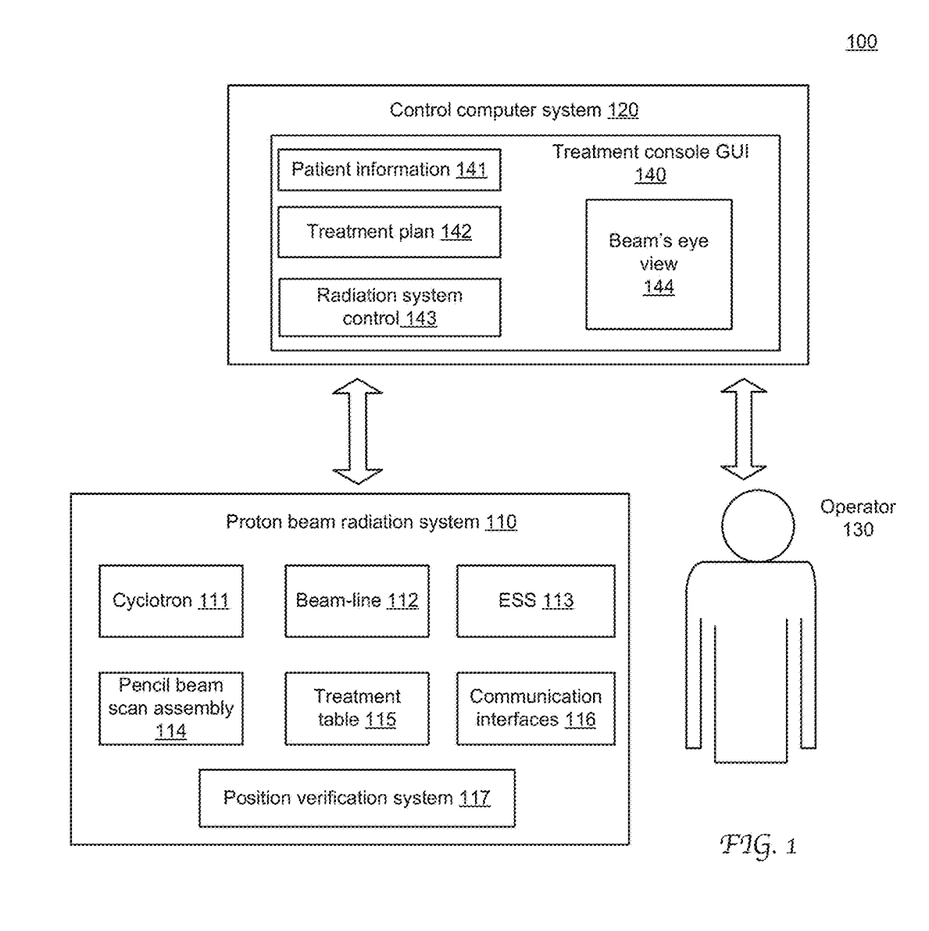
FIG. 1 illustrates an exemplary system for proton radiation therapy enabling anatomical representations of an irradiation target to be visually presented to a user through a treatment console GUI in accordance with an embodiment of the present disclosure.

FIG. 1 illustrates an exemplary system 100 for proton radiation therapy enabling anatomical representations of an irradiation target volume to be visually presented to a user through a treatment console GUI 140 in accordance with an embodiment of the present disclosure. The system 100 includes a proton beam radiation system 110 and a control computer system 120 through which an operator-user 130 can control and monitor the radiation system 110.

The proton beam radiation system 110 primarily includes a cyclotron 111, a beam-line 112, an energy selection system (ESS) 113, a pencil beam scan assembly 114, a treatment table 115, various control/communication interfaces 116 and a patient position verification system (PVS) 117. The cyclotron 111 operates to generate a beam of protons extracted from an internal ion source located in the center of the cyclotron 111. The proton beam exiting the cyclotron has a fixed level of energy. The protons in the beam are accelerated and directed under the interplay of the external electrical and magnetic fields. The ESS 113 includes energy slits, bending magnets and focusing magnets, and is used to remove protons with excessive energy or with deviations in angular direction from the beam.

The proton beam is tuned and delivered to an irradiation target via a beam transportation system. At the end of the beam transport system, a gantry associated with an irradiation nozzle delivers the beam onto the irradiation target (e.g. a tumor inside the body of a patient) in a fixed position supported by the treatment table 115 during operation. The beam energy is modified to an appropriate therapeutic level as dictated by the depth of the irradiation target within the body of the patient.

The beam-line 112 is composed of a series of interconnecting tubes, and often guides the beam through multiple chambers, rooms, or even floors of a building, and finally to an irradiation target inside a patient placed on the treatment table 115. The components 111-115 in the radiation system 110 communicate with the control computer system 120 through the various communication interfaces 116, such as send signals representing the respective operational situations of the components 111-115, and receive control signals from the control computer 120. The position verification system 117 includes an imaging device and, in conjunction with its control software installed in the control computer system 120, operates to generate images (e.g., to verify patient positioning). Such an image is typically compared (e.g., overlaid or aligned) with a corresponding reference image to assess accuracy of positioning for treatment. If the comparison indicates that re-positioning is needed, the treatment table 115 can be adjusted to the desired treatment position. The imaging device can generate orthogonal X-ray images or Cone beam computed tomography (CBCT) images for example. It will be appreciated that reference images can be obtained before an treatment and independent of the position verification system 117. The reference images may be MRI, CT, and CBCT images, etc.

The control computer system 120 is installed with a treatment console program operable to acquire and present the statuses as well as control the operations of the components 111-116 in the radiation system 110. The treatment console program renders an on-screen graphical user interface (GUI) 140 that integrates the fields of patient information 141, treatment plan 142, radiation system control 143, and beam's eye view (BEV) 144. Through the GUI 140, the operator 130 selects and loads a treatment plan made for a specific patient. According to the present disclosure, the BEV field 144 can present the overlay of an acquired image and the corresponding reference images at user's choice. The comparison can be used to verify validity of a therapy session.

The corresponding patient profile and the treatment plan description are displayed in the fields of 141 and 142. The operator 130 sends commands through the GUI 140 to control the operations of various components of the radiation system 110, such as move the treatment table 115 to a default position, or commence the irradiation process according to the selected treatment plan. In turn, the information on the radiation system 110 is acquired and displayed in the GUI 140, such as the current proton beam energy, the treatment table position, the gantry position, etc.

It will be appreciated by those skilled in the art that the proton beam radiation system 110 and the control computer system 120 each include various other functional components not shown in FIG. 1. Further, each component in the system 110 and 120 includes various other functional constituent parts not described above with reference to FIG. 1.

According to the present disclosure, a beam's eye view (BEV) showing the anatomy of a target volume and nearby risk organs is rendered for display in the dedicated BEV field 144. In an "online" mode, the on-screen BEV rendition is dynamically coordinated with the contemporaneous irradiation progress during a treatment session. In an "offline" mode, a BEV is rendered independent of the operational statuses of the associated radiation system. In either mode, the BEV field can be used to present 3D volumetric images, 2D images, spot maps or combination of images for purposes of comparison.

The target volume referred to herein may be a gross tumor volume (GTV), clinical target volume (CTV), planning target volume (PVT), etc. In some embodiments, the BEVs are simulated two-dimensional (2D) or three-dimensional (2D) images that are generated prior to a radiation therapy session.

During an irradiation session, the control computer system 120 communicates with the radiation system 110 in real-time such that a set of BEVs are dynamically rendered to provide a real-time visualization of the irradiation progress in an anatomical context. In some radiation systems, protons are delivered to a target volume by pencil beam scanning in a series of layers. Accordingly, a set of BEVs, with each corresponding to a scan layer, are sequentially rendered in the field 144 in synchronization with the layer scanning process. Particularly, the currently displayed BEV corresponds to the currently irradiated layer. Each BEV may be labeled with a layer index.

The present disclosure is not limited to any specific technique or method of realizing synchronization between the BEV renditions and the irradiation layer scanning processes. In one embodiments, signals indicative of proton beam energy level transitions, which are associated with scanning layer transitions, are provided to the treatment console program and used to trigger BEV display transitions in real-time, as will be described in greater detail below.

In one embodiment, a moving on-screen visual object that dynamically represents the instant location of the beam relative to the irradiation target is rendered upon a currently displayed BEV. Further, the area that has been irradiated is presented in a different format from the rest of the BEV to show the progress of the irradiation delivery on the current layer.

The BEV images according to the present disclosure serve a variety of purposes during a treatment session. In one embodiment, the BEV images allow an operator or a software program to monitor the position and/or accuracy of the target volume over the course of a treatment session. For example, the system can check for position difference before starting the beam and adjust patient position accordingly.

After an irradiation session, the dynamic visualizations rendered during the session can be played back in response to user requests for review. A user is allowed to control the playback speed during a review. A slider control object is optionally used for the playback presentation to allow the user to navigate quickly back and forth in the play sequence. A user can also select and export a play sequence as a standard video file.

Prior to an irradiation session, a set of BEVs are displayed in the field 144 in an offline mode to help the operator verify the prescribed treatment plan to be executed. The BEVs provide a safety check to verify that the irradiation target location, size and shape match the expected anatomy of the current patient and irradiation target. This aids the operator in confirming treatment indications and irradiation target prior to the irradiation delivery session. As an additional confirmatory check, an operator is required to submit an affirmative answer to a question cue "Am I treating the right target?" before being allowed to commence the irradiation session.

The present disclosure is not limited to any specific manner that a set of BEV images for an irradiation target are presented to an operator. Prior to or subsequent to an irradiation session, an operator can select to view individual layers in a preset sequence (e.g., in a slide show) or to randomly access any desired layer. In one embodiment, user manipulations on the BEV display mode are blocked when irradiation is in progress. A BEV is displayed with or without treatment layer information through Boolean add-in or subtract out. Further, BEVs are presented as 2D layer images or an integrated 3D volume image at operator selection. The images of multiple layers are displayed as a stack to provide a comprehensive visualization of a PVT or an actually irradiated volume.

The BEV field 144 includes various visual objects corresponding to BEV display options, such as 2D, 3D, layer selection, slideshow, video play, view angles, etc. In one embodiment, the treatment console GUI 140 has multiple GUI windows or tabs, such as a treatment setup window, a treatment irradiation window, or a patient verification window. A BEV field is configured to appear in a consistent screen location on each window.

After an irradiation session, an actually irradiated volume is derived based on the actual energy levels of the delivered proton beam, the delivered dosage at each energy level, and/or the motion paths of the scanning nozzle. An actually irradiated volume can be different from the corresponding planning target volume, especially in case of an interrupted or partial treatment. In such case, a difference volume (or residual volume) is computed and visually presented in the BEV field 144 as a 3D volume image or as 2D slice images. Moreover, the actually delivered dosage for each layer is computed and individually displayed in the corresponding BEV. The visualization features described herein can be respectively implemented in any suitable techniques, methods, processes, models, algorithms that are well known in the art. For instance, the actually treated area is marked by a different color from the planning target volume on screen.

Various techniques and processes of generating simulated images representing anatomical structures of a target volume and slices thereof that are well known in the art can be utilized for purposes of practicing the present disclosure. In one embodiment, a BEV image is a digitally reconstructed radiograph (DRR) which may be created from a computed tomography (or CT) data set, a megavoltage computed tomography (MVCT) data set, a magnetic resonance imaging (MRI) data set, 3D images of high contrast objects using rotating C-arms, or images captured by the imaging device of the PVS (e.g., 117 FIG. 1) etc. A PVS may generate DRR images before or during a treatment session for BEV display.

Figure 2A:
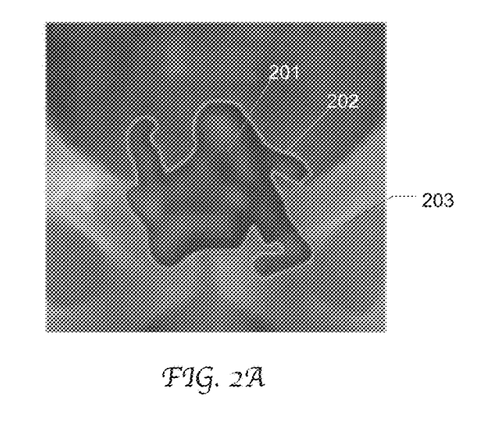
FIG. 2A is an exemplary on-screen DRR image rendered as a Beam's Eye View (BEV) in a treatment console GUI in accordance with an embodiment of the present disclosure.

An on-screen outline contouring a target volume can be rendered on a BEV to show the boundary of the target volume. FIG. 2A is an exemplary on-screen DRR image rendered as a BEV in a treatment console GUI in accordance with an embodiment of the present disclosure. In FIG. 2A, the DRR shows the target volume 201 for irradiation (the foreground), the outline 202 of the target volume 201, and the adjacent risk organs 203 (the background). The outline 202 delineating the target volume may be defined manually by a specialist, through an automatic delineation process provided by a software program, or a combination thereof.

Figure 2B:
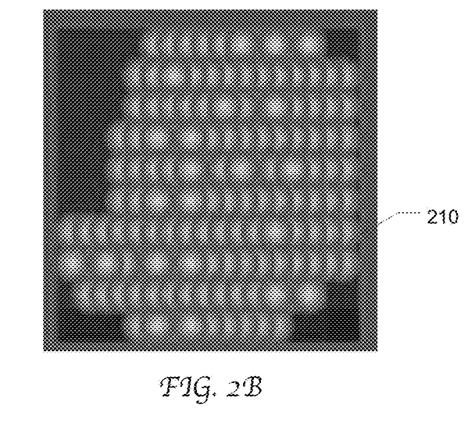
FIG. 2B is an exemplary on-screen planned spot map rendered as a BEV in a treatment console GUI in accordance with an embodiment of the present disclosure.

FIG. 2B is an exemplary planned spot map rendered as a BEV in a treatment console GUI in accordance with an embodiment of the present disclosure. Each spot 210 represents an anticipated beam delivery location on the irradiation target based on a treatment plan. The illustrated planned spot map provides a collapsed view of the anticipated irradiation locations across all the layers of the target volume. A spot map for an individual layer may also be presented as an on-screen BEV to a user.

Figure 2C:
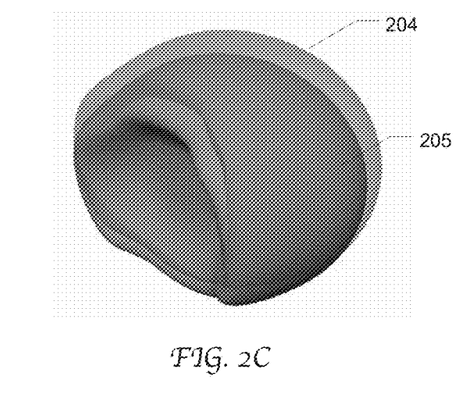
FIG. 2C is an exemplary on-screen 3D anatomical image of a target volume rendered as a BEV in a treatment console GUI in accordance with an embodiment of the present disclosure.

FIG. 2C is an exemplary on-screen 3D anatomical image of a target volume rendered as a BEV in a treatment console GUI in accordance with an embodiment of the present disclosure. In this example, the 3D image shows both the PVT 204 and the actually irradiated volume 205 which is a portion of the PVT 204. FIG. 2C provides a visual connection from the planning stage to the actual treatment. Responsive to a user selection, a 3D image of a PVT, the actually irradiated volume or a difference thereof (the residual volume) is individually displayed (not shown).

Figure 2D:
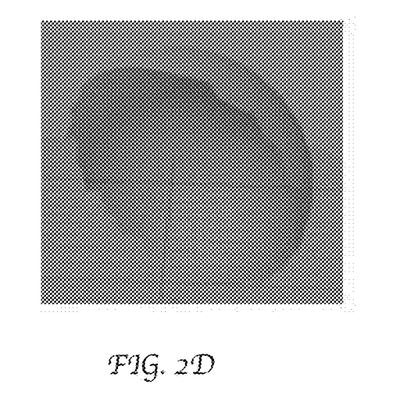
FIG. 2D is an exemplary 3D anatomical image of a residual volume rendered as a BEV in a treatment console GUI in accordance with an embodiment of the present disclosure.

FIG. 2D is an exemplary on-screen 3D anatomical image of a residual volume after an irradiation session that is rendered as a BEV in a treatment console GUI in accordance with an embodiment of the present disclosure. Responsive to a user selection, a 2D image of the residual (planned but not irradiated) area in each layer is individually displayed as well.

A user can manipulate the presentation of a 3D anatomical image (e.g., FIGS. 2C and 2D) in any suitable manner, such as to change the view angle, camera perspective, transparency, or zoom, etc. In one embodiment, once irradiation starts, the on-screen presentation automatically switches back to a field view that visualizes the location and orientation of the irradiation target from the viewpoint of the scanning nozzle.

Figure 3:
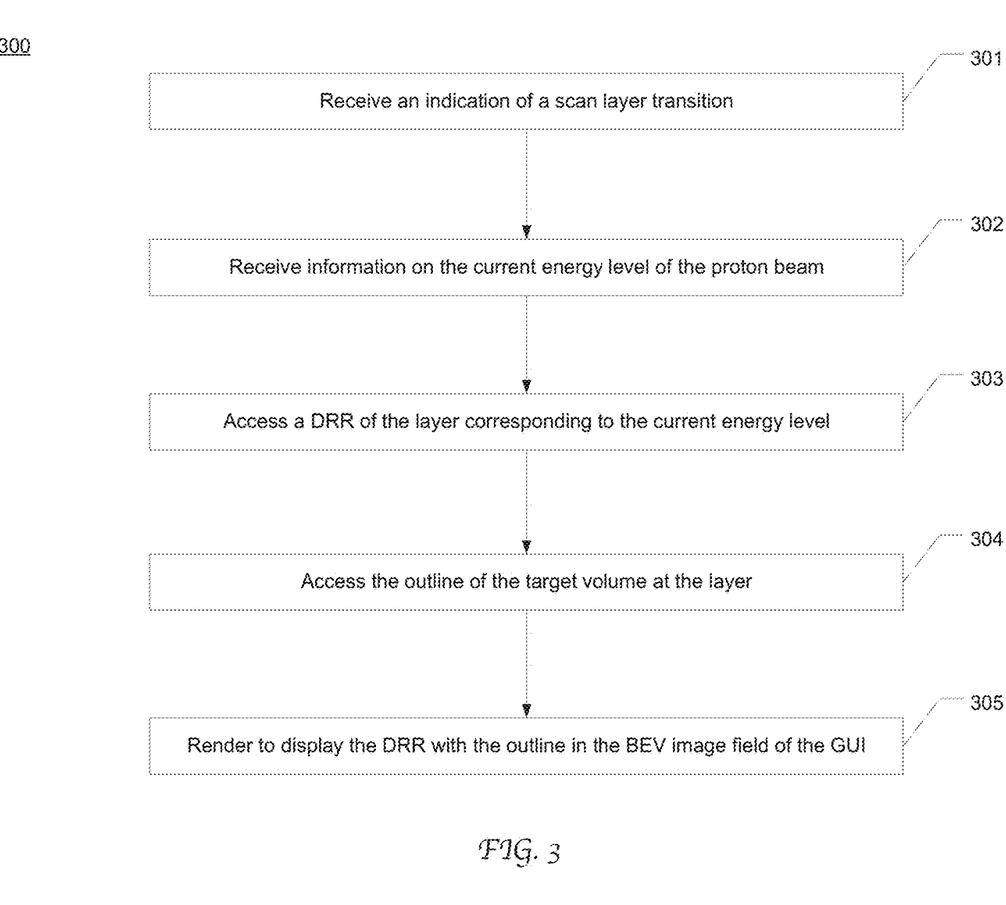
FIG. 3 is a flow chart depicting an exemplary computer implemented method of providing real-time visualization of a pencil beam irradiation session in an anatomical context in accordance with an embodiment of the present disclosure.

FIG. 3 is a flow chart depicting an exemplary computer implemented method 300 of providing real-time on-screen visualization of a pencil beam irradiation session in an anatomical context in accordance with an embodiment of the present disclosure. The method 300 is implemented as an integral part of the treatment console program installed in a control computer, e.g., 120 in FIG. 1. During an irradiation session, at 301 of FIG. 3, a signal indicating a transition in an irradiation scan layer is received. As prescribed in a treatment plan, each layer of the target volume is associated with a proton beam energy level. Thus, the signal may be generated in response to the transition in the proton beam energy. Alternatively, the signal may be generated based on the motion path of the scanning nozzle, or by any other suitable manner.

At 302, the information on the current energy level of the proton beam is received. At 303, based on the current energy level, a currently irradiated layer is identified and the DRR representing the layer is accessed. At 304, the outline of the target volume at the current layer is accessed. At 305, the DRR and the outline are rendered for display in the BEV image field of the treatment console GUI. The foregoing process 301-305 is repeated each time a beam energy transition occurs during an irradiation session.

Figure 4:
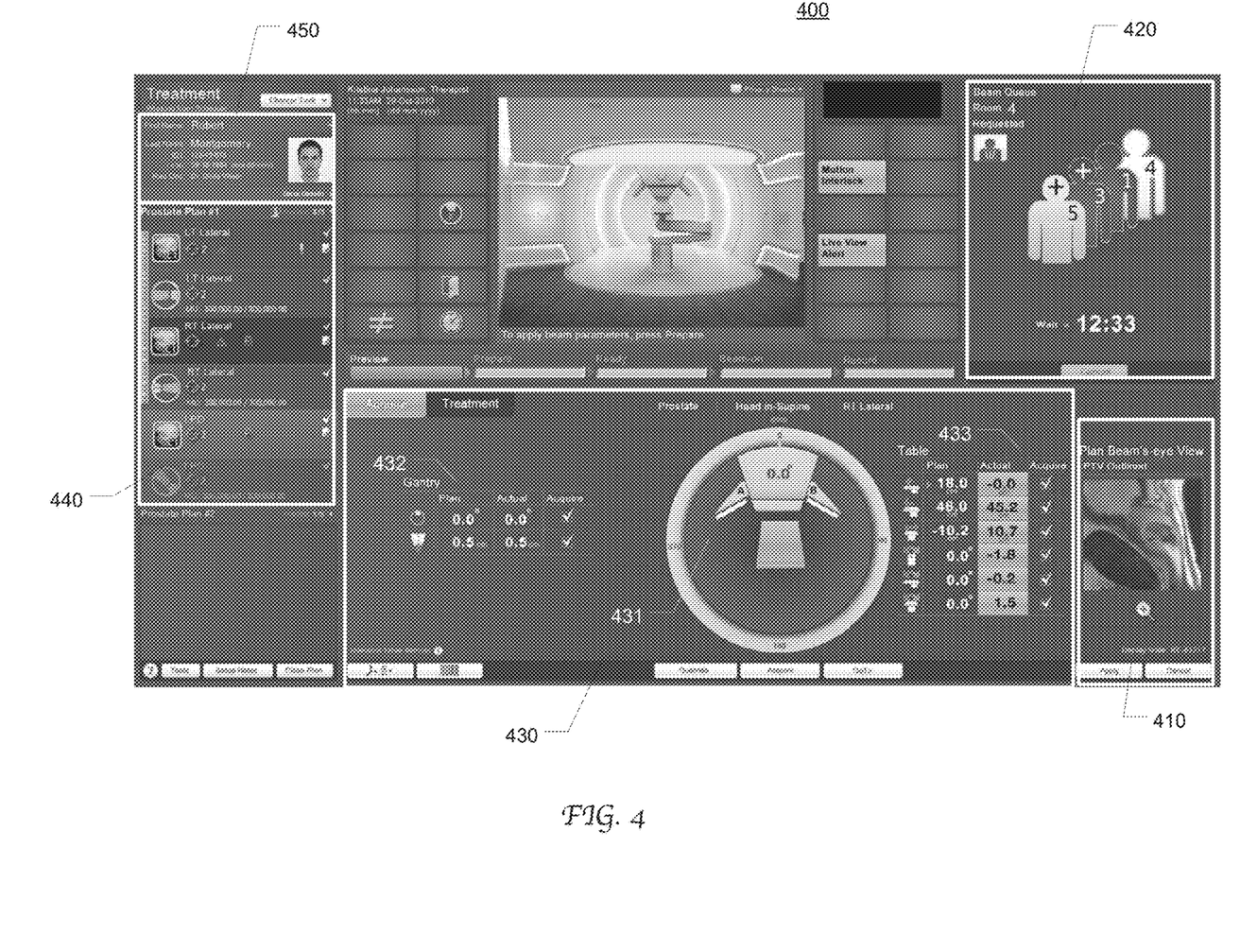
FIG. 4 is an exemplary treatment console GUI having an image field for providing anatomical visualization of an irradiation target in accordance with an embodiment of the present disclosure.

FIG. 4 is an exemplary on-screen treatment console GUI 400 having an image field (or window) 410 for presenting anatomical visualization of target volumes "BEVs" in accordance with an embodiment of the present disclosure. The GUI 400 integrates a BEV field 410, a beam request field 420, a radiation system control field 430, a treatment plan field 440 and a patient information field 450.

The BEV field 410 displays the beam's view point as well as various other types and forms of anatomical representations of a target volume during, before or after an irradiation session, as described in greater detail with reference to FIGS. 1-3. The beam request field 420 is designed to provide a user interface for visualizing and controlling the usage and allocation of a therapy system shared by multiple treatment stations. Specifically, the beam request field 420 allows a user to visualize a beam request queue, request the shared therapy beam for treatment, estimate when a beam request will be fulfilled, and cancel a beam request, etc.

The radiation system control field 430 displays the statuses of various system components and receives user input to control their operations. In this example, the radiation system control field 430 shows a diagram 431 graphically presenting the locations of the gantry and treatment table relative to each other. Also included are the actual and planned values of positional parameters related to the gantry and the treatment table (432 and 433). The treatment plan field 440 presents the assigned values of assorted parameters as prescribed in the treatment plan. The patient information field 450 presents the patient profile associated with the treatment plan that is described in field 440. The present disclosure is not limited to any specific configuration, design, or pattern of a treatment console GUI. It will be appreciated that a treatment console GUI in accordance with the present disclosure can include any other suitable information, arrangement of windows, visual objects, functions and can be implemented in any suitable method that is well known in the art.

Figure 5:
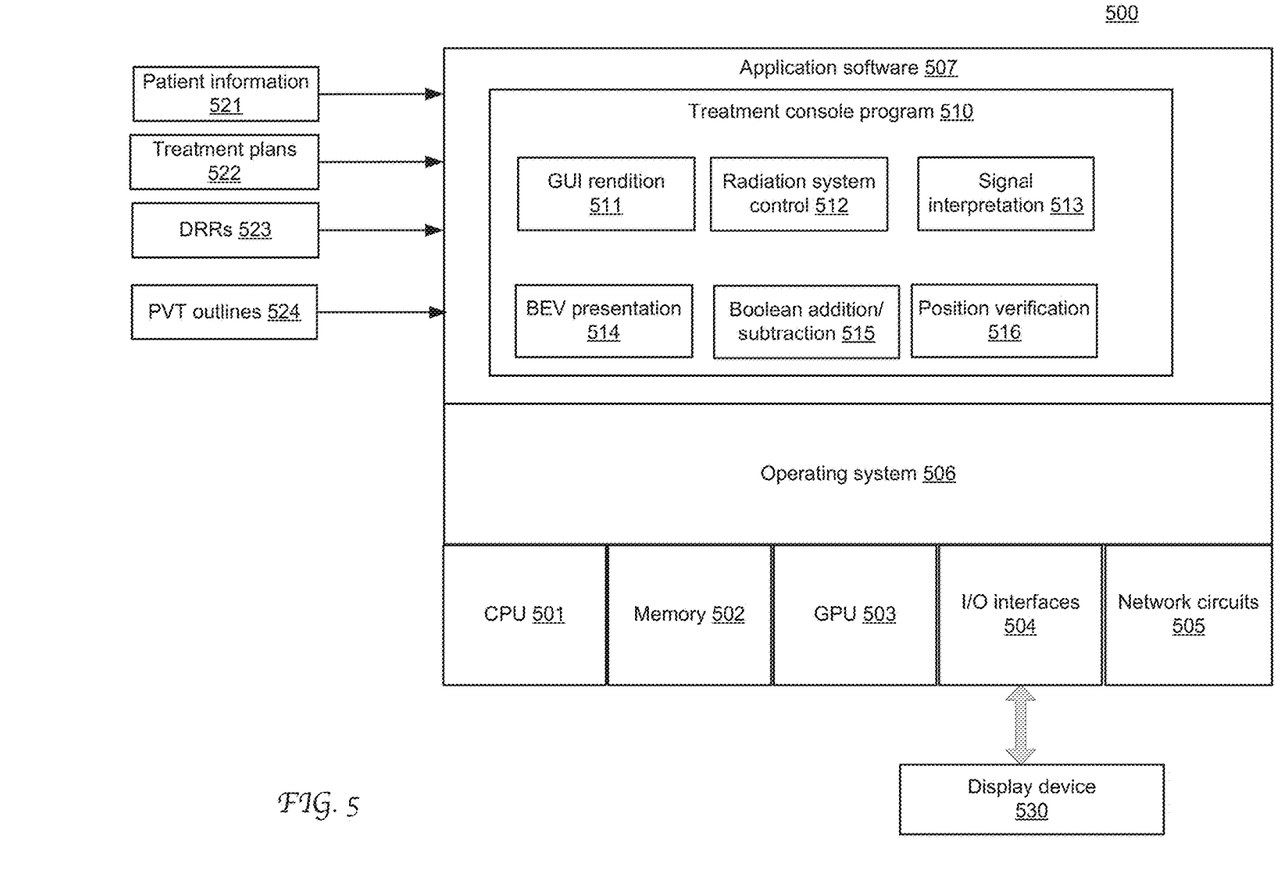
FIG. 5 is a block diagram illustrating an exemplary computing system including a treatment console program capable of rendering BEVs for proton radiation therapy in accordance with an embodiment of the present disclosure.

FIG. 5 is a block diagram illustrating an exemplary computing system 500 including a treatment console program 510 capable of rendering BEVs for proton radiation therapy in accordance with an embodiment of the present disclosure. The computing system 500 includes a central processing unit (CPU) 501, system memory 502, a graphics processing unit (GPU) 503, I/O interfaces 504, network circuits 505, an operating system 506 and application software 507. The application software 507 includes the treatment console program 510 stored in the memory 502. BEV images, target volume outlines, treatment plans, and patient information to be processed and presented by the treatment console program 510 (as shown in FIG. 4) are stored in a local or remote secondary storage device (not shown) associated with the computing system 500. The computing system 500 is coupled to a proton beam radiation system through a communication channel, as shown in FIG. 1. The computing system 500 is equipped with a display device 530 coupled to the processors 501 and 503 through an I/O interface 504.

In the illustrated example, the treatment console program 510 includes a GUI rendition module 511, a radiation system control module 512, a signal interpretation module 513, a BEV presentation module 514, a Boolean addition/subtraction module 515, and a position verification module 516. Patient information 521, treatment plans 522, DRRs 523 and PVT outlines 524 are determined independent of the console program 510 and provided to the program 510 as customized input. When incorporating configuration input as well as the customized input 521-524, the treatment console program 510 can render a treatment console GUI as a user interface with the proton beam radiation system. The radiation system control module 512 generates control indications to control the operations of the proton beam radiation system based on a prescribed treatment plan or a user input.

The signal interpretation module 513 interprets signals transmitted from the proton beam radiation system and generates indications to control various actions defined in the treatment console program 510. For example, the signal interpretation module 513 translates a proton beam energy transition signal into an indication that triggers the BEV presentation module 514 to change to display another layer, as described above. The BEV presentation module 514 adapts a set of DRRs to BEVs for on-screen presentation in a user-selected form and display mode. The BEV field displays a PVT, an actually irradiated volume, a residual volume, a slice of a target volume. The Boolean addition/subtraction module 515 analyzes a PVT and the corresponding actually irradiated volume to derive a delta volume therefrom as well as determine the dose accumulation on each planned layer.

The position verification module 516 controls the operations of the imaging device to acquire images to aid visualizations that can be used for multiple purposes (e.g., to review patient setup, to match acquired images with reference images to verify treatment position, to correct positioning errors before treatment, track the patient during beam delivery).

The treatment console program 510 may perform various other functions as discussed in detail with reference to FIGS. 1-4. As will be appreciated by those with ordinary skill in the art, the treatment console program 510 can be implemented in any one or more suitable programming languages that are known to those skilled in the art, such as C, C++, Java, Python, Perl, C#, SQL, etc.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A computer implemented method of providing visual representations during radiation therapy processes, said method comprising:

during an irradiation operation of a particle radiation apparatus in a radiation therapy process, rendering an on-screen graphical user interface (GUI) for display on a display device of a computer system adapted to be communicably coupled to said particle radiation apparatus, wherein said on-screen GUI is configured to:
present patient information pertinent to said radiation therapy process; and
present operational statuses of said particle radiation apparatus;
accessing an image comprising an anatomical representation of a target volume, wherein said target volume is defined for said radiation therapy process, wherein said image is generated prior to said radiation therapy process, wherein said anatomical representation represents a layer being irradiated by said particle radiation apparatus, wherein said layer of said target volume is associated with a respective energy level of a particle beam in said particle radiation apparatus;
receiving an indication of an operational status regarding said irradiation operation from said particle radiation apparatus during said irradiation operation; and
responsive to said indication, rendering said image for display within said on-screen GUI in synchronization with said particle radiation apparatus irradiating said layer at said respective energy level.

2. The computer implemented method of claim 1 further comprising:
accessing a plurality of images comprising said image, wherein said plurality of images are generated prior to said radiation therapy process, wherein each of said plurality of images represents an anatomical representation of a respective layer being irradiated by said particle radiation apparatus, wherein said plurality of images are associated with respective energy levels of said particle beam; and
rendering said plurality of image for display within said on-screen GUI in synchronization with said particle radiation apparatus irradiating said plurality of layers at said respective energy levels.

3. The computer implemented method of claim 1, wherein said indication indicates that said particle radiation apparatus transitions to irradiate said layer from another layer.

4. The computer implemented method of claim 1 further comprising comparing said image with a reference image to verify validity of a therapy session associated with said radiation therapy process.

5. The computer implemented method of claim 1, wherein said image is a digitally reconstructed radiograph (DRR), and wherein said DRR comprises a representation of anatomical structures surrounding said target volume.

6. The computer implemented method of claim 1 further comprising rendering a graphical representation of a boundary of said target volume for display within said image.

7. The computer implemented method of claim 1, wherein said anatomical representation is a three-dimensional representation of said target volume.

8. The computer implemented method of claim 1, wherein said particle beam is a proton beam, and further comprising:
   determining an actually irradiated volume as a result of said radiation therapy process;
   deriving a difference between said target volume and an actually irradiated volume; and
   subsequent to said radiation therapy process, rendering a graphical representation of said difference for display within said on-screen GUI.

9. A non-transitory computer-readable storage medium embodying instructions that, when executed by a processing device, cause the processing device to perform a method of facilitating visualization of proton beam therapy for users, said method comprises:
   rendering an on-screen graphical user interface (GUI) for display on a display device operable to be communicably coupled to a proton therapy apparatus during an irradiation operation of said proton therapy apparatus in a radiation therapy process, wherein said proton therapy apparatus is configured to irradiate a plurality of layers of an irradiation target volume by using a proton beam during said irradiation operations;
   accessing a plurality of images generated prior to said radiation therapy process, wherein each image of said plurality of images comprises an anatomical representation of a respective layer of said plurality of layers, wherein said plurality of images are associated with respective energy levels of said proton beam; and
   during said irradiation operation, receiving an indication from said proton therapy apparatus indicating that said proton therapy apparatus starts to irradiate a corresponding layer of said irradiation target volume at a corresponding energy level; and
   during said irradiation operation, automatically rendering a select image from said plurality of images within said on-screen GUI in response to said indication, wherein said select image comprises an anatomical representation of said corresponding layer.

10. The non-transitory computer-readable storage medium of claim 9, wherein said plurality of images are digitally reconstructed radiographs (DRRs) that are generated based on a computerized tomography (CT) data set.

11. The non-transitory computer-readable storage medium of claim 9, wherein said method further comprises rendering another image selected from said plurality of images responsive to a user selection prior to or subsequent to said therapy session.

12. The non-transitory computer-readable storage medium of claim 9, wherein said indication is generated responsive to a transition of an energy level of said proton beam.

13. The non-transitory computer-readable storage medium of claim 9, wherein said method further comprises:
   generating a Boolean addition of said plurality of images in response to a user request; and
   rendering a graphical representation of said Boolean addition for display within said on-screen GUI.

14. The non-transitory computer-readable storage medium of claim 9, wherein said method further comprises:
   determining an actually irradiated volume resulted from said therapy session;
   deriving a difference between said actually irradiated volume and said irradiation target volume, wherein said irradiation target volume is a planning target volume; and
   rendering a graphical representation of said difference for display within said on-screen GUI.

15. The non-transitory computer-readable storage medium of claim 9, wherein said select image is associated with a graphical object representing a boundary of said irradiation target volume at said corresponding layer, and wherein further said boundary is determined via an automated process.

16. The non-transitory computer-readable storage medium of claim 9, wherein said method further comprises rendering a three-dimensional graphical object representing said irradiation target volume for display within said on-screen GUI.

17. A system for controlling particle radiation therapy comprising:
   a proton therapy apparatus configured to irradiate a plurality of layers of an irradiation target volume by using a proton beam during an irradiation operation in a radiation therapy process; and
   a control system communicably coupled to said particle therapy apparatus and configured to control said particle therapy apparatus responsive to user input, wherein said control system comprises:
   a processor;
   a display device coupled to said processor; and
   memory coupled to said processor and said display device and comprising instructions that, when executed by said processor, cause the processor to perform a method of facilitating visualization of radiation delivery processes performed by said proton therapy apparatus, said method comprising:
   rendering an on-screen graphical user interface (GUI) for display on said display device;
   during said radiation therapy process, accessing a plurality of images generated prior to said radiation therapy process, wherein each image of said plurality of images comprises an anatomical representation of a respective layer of said plurality of layers; and
   during said irradiation operation, receiving an indication from said proton therapy apparatus that said proton therapy apparatus starts to irradiate a corresponding layer of said irradiation target volume in said irradiation operation;
   responsive to said indication, automatically rendering a select image from said plurality of images within said on-screen GUI during said irradiation operation, wherein said select image comprises an anatomical representation of said corresponding layer, wherein each layer of said plurality of layers is associated with a respective energy level of said proton beam during said irradiation operation.

18. The system of claim 17, wherein said proton therapy apparatus comprises:
   a cyclotron configured to generate said proton beam;

an energy selection system configured to select an energy level for said proton beam;
a pencil beam scanning system configured to direct said proton beam to said irradiation target volume; and
a beam transportation line configured to route said proton beam from said cyclotron to said pencil beam scanning system.

19. The system of claim 17, wherein said method further comprises:
determining an actually irradiated volume resulted from said therapy session;
deriving a difference between said actually irradiated volume and said irradiation target volume, wherein said irradiation target volume is a planning target volume; and
rendering a graphical representation of said difference for display within said on-screen GUI.

20. The system of claim 17, wherein said method further comprises automatically rendering a graphic object on said select image, and wherein said graphic object represents a boundary of said irradiation target volume at said corresponding layer.

* * * * *